United States Patent [19]

Munakata et al.

[11] Patent Number: 4,786,476
[45] Date of Patent: Nov. 22, 1988

[54] GAS SENSOR ELEMENT USING POROUSLY FIRED MASS OF TITANIA

[75] Inventors: Fumio Munakata; Masayuki Touda, both of Yokosuka; Masaaki Uchida, Yokohama; Fumio Yukawa, Yokosuka, all of Japan

[73] Assignee: Nissan Motor Co., Ltd., Yokohama, Japan

[21] Appl. No.: 886,080

[22] Filed: Jul. 16, 1986

[30] Foreign Application Priority Data

Jul. 17, 1985 [JP] Japan .............................. 60-155889
Aug. 23, 1985 [JP] Japan .............................. 60-184078

[51] Int. Cl.$^4$ ............................................ G01N 27/46
[52] U.S. Cl. ..................................... 422/98; 204/421; 204/424
[58] Field of Search ........................... 204/421–429; 422/98

[56] References Cited

U.S. PATENT DOCUMENTS

| | | | |
|---|---|---|---|
| 3,576,730 | 4/1971 | Spacil | 204/424 |
| 3,751,968 | 8/1973 | Loh et al. | 422/98 |
| 4,045,178 | 8/1977 | Okinaka et al. | 422/98 |
| 4,058,368 | 11/1977 | Svenson et al. | 422/98 |
| 4,242,302 | 12/1980 | Kitamura et al. | 422/98 |
| 4,387,165 | 6/1983 | Youngblood | 422/98 |
| 4,416,763 | 11/1983 | Fujishiro | 204/412 |
| 4,601,883 | 7/1986 | Sekido et al. | 422/98 |

OTHER PUBLICATIONS

Patents Abstracts of Japan, vol. 4, No. 95, Jul. 1980, p. 18, Japanese 55-57143.

*Primary Examiner*—T. Tung
*Attorney, Agent, or Firm*—Foley & Lardner, Schwartz, Jeffery, Schwaab, Mack, Blumenthal & Evans

[57] ABSTRACT

The invention relates to a gas sensor element which utilizes a change in the electric resistance of a porously fired $TiO_2$ layer. To improve the speed of response of the gas sensor element, and also to strengthen the adhesion of the fired $TiO_2$ layer to a ceramic substrate, at least one kind of metal oxide which hardly undergoes solid phase reaction with $TiO_2$ and serves as a sintering suppressing agent, such as $Er_2O_3$, $Sm_2O_3$ and/or $In_2O_3$, is added to $TiO_2$ in advance of firing. The speed of response is further enhanced by the addition of at least one kind of noble metal such as Pt and/or Rh to $TiO_2$ together with the sintering suppressing oxide(s).

17 Claims, 3 Drawing Sheets ately sintered substrate is insufficient so that partial peeling will occur at the interface during practical operations of the gas sensor.

GAS SENSOR ELEMENT USING POROUSLY FIRED MASS OF TITANIA

BACKGROUND OF THE INVENTION

This invention relates to a gas sensor element of the type using a change in electric resistance of a transition metal oxide, and more particularly to a gas sensor element having a porously fired mass of titanium dioxide.

In one type of conventional gas sensor the sensitive material is a transition metal oxide which undergoes a change in its electric resistance with the content of a specific component in an environmental gas atmosphere. In practical oxygen sensors of this type titanium dioxide is prevails as the sensitive transition metal oxide, and it is usual to use titanium dioxide (titania) in the form of a microscopically porously fired layer so that the gas subject to measurement may freely permeate into and through the mass of the metal oxide.

A titania type oxygen sensor is of use as an exhaust sensor in an air/fuel ratio feedback control system for an internal combustion engine because the electric resistance of the titania layer in the sensor exposed to the exhaust gas exhibits a sharp change if the air/fuel ratio in the engine combustion chambers changes across the stoichiometric ratio where the excess air factor is 1.0. To enhance the sensitivity and the speed of response of the oxygen sensor it has been proposed to add a small amount of a noble metal such as platinum or rhodium as described in, for example, Japanese patent application primary publication No. 53-11226. To expand the applicability of titania type gas sensors, U.S. Pat. No. 4,416,763 discloses an air/fuel ratio detecting device for use in engine exhaust gases, which is an integrated combination of a titania type oxygen sensor element and an oxygen ion pump using an oxygen ion conductive solid electrolyte such as zirconia. In this device the resistance of the titania layer exhibits a sharp change in response to a change in the air/fuel ratio in the engine across a nonstoichiometric ratio which is above or below the stoichiometric ratio depending on the polarity of a DC current supplied to the oxygen ion pump. Therefore, this device is applicable to both lean-burn engines and rich-burn engines.

In conventional titania type gas sensors it is usual that the functional part including a titania layer and electrode layers is constructed as a laminate formed on a ceramic substrate by a so-called thick-film technique. To enhance the strength of adhesion of the titania layer to the substrate it is favorable to first prepare a green laminate including the substrate in green state and then fire the green laminate at a relatively high temperature such as about 1300°–1400° C. to thereby accomplish simultaneous sintering of the substrate and the overlying layers. In such cases, however, the fired titania layer often has an excessively tightly sintered structure which is low in permeability to gas molecules presumably by reason of the very rapid growth of titania particles under sintering. With such structure of the fired titania layer it is difficult to satisfy the desire for high speed of response of the gas sensor. It is possible to prevent excessive sintering of the titania layer and resultant low permeability of the same layer by first sintering the substrate alone at a sufficiently high temperature such as about 1400° C. or above, then forming a green laminate including a titania layer on the sintered substrate and finally firing the whole assembly at a relatively low temperature such as about 1200° C. or below. In this case, however, it is likely that the strength of adhesion of the fired titania layer to the precedingly sintered substrate is insufficient so that partial peeling will occur at the interface during practical operations of the gas sensor.

SUMMARY OF THE INVENTION

It is an object of the present invention to provide an improved gas sensor element having a fired mass of titania, in which the fired titania mass is sufficiently high in permeability to gas molecules and accordingly is high in the speed of response to a change in the amount of a specific component of an environmental gas atmosphere and, besides, in which the strength of adhesion of the fired titania mass to the substrate is high enough to avoid the possibility of peeling phenomena during practical use of the gas sensor element.

A gas sensor element according to the invention has, as a sensitive part which undergoes changes in its electric resistance, a porously fired mass comprising titanium dioxide as the principal material thereof and a pair of electrodes attached to the fired mass of titanium dioxide so as to measure the electric resistance of a predetermined section of that fired mass. The improvement according to the invention resides primarily in that the fired mass of titanium dioxide comprises at least one additional metal oxide which hardly undergoes solid phase reaction with titanium dioxide and serves as a sintering suppressing agent.

The sintering suppressing agent can be selected from oxides of rare earth elements and some metal oxides having high melting points which are higher than the melting point of titanium dioxide. It is preferred to use $Er_2O_3$, $Sm_2O_3$ and/or $In_2O_3$ as the sintering suppressing agent, and it is suitable that the total amount of the sintering suppressing agent is from 0.01 to 10 mol % of $TiO_2$.

The sintering suppressing agent is added to and mixed with a titania powder as the raw material of the sensitive part of the gas sensor element. Usually the mixed powder is applied onto the surface of a substrate as a paste. At the subsequent firing process the growth of titania particles is suppressed by the coexisting metal oxide, so that the fired titania mass has good permeability to gas molecules even though the firing temperature is considerably higher than 1200° C. Good permeability of the fired titania mass leads to high speed of response of the same mass to a specific change in the composition of the permeating gas. Since excessive sintering of titania particles is prevented by the addition of the sintering suppressing oxide, it is possible to produce the gas sensor element by firing a green laminate including a green substrate at a temperature high enough to achieve strong adhesion of the fired titania layer to the simultaneously fired substrate.

Further improvement can be produced in the speed of response of a gas sensor element according to the invention by adding at least one noble metal of the platinum group to titania as the material of the sensitive part besides the sintering suppressing agent. It is preferred to use platinum and/or rhodium which amount, in total, to 0.01–10 mol % of $TiO_2$.

DESCRIPTION OF THE PREFERRED EMBODIMENTS

Figure 1:
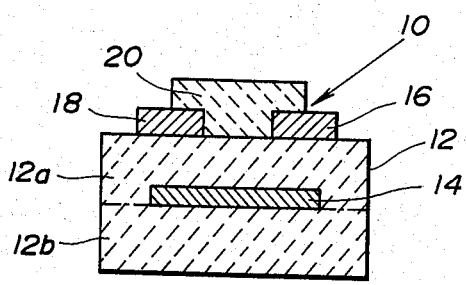
FIG. 1 is a schematic illustration of a gas sensor element according to the invention in a sectional view.
Figure 2:
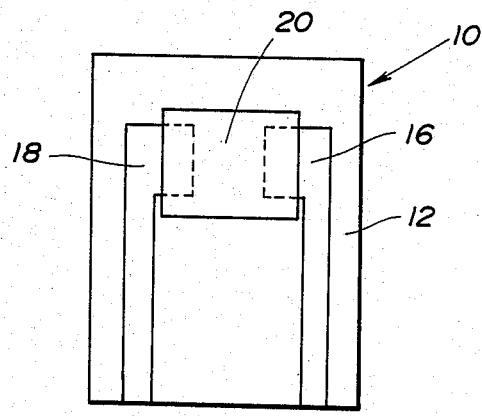
FIG. 2 is a plan view of the gas sensor element of FIG. 1.

FIGS. 1 and 2 show the construction of a gas sensor element 10 according to the invention by way of example. The sensor element 10 has a substrate 12 made of an electrically insulating and heat-resistant material, such as sintered alumina, as a structurally basic part of the element. In most cases a heater 14 such as a film or filament of platinum is embedded in the substrate 12. In the illustrated case the substrate 12 is prepared by lamination of two sheets 12a and 12b for insertion of the heater 14.

A pair of electrode layers 16 and 18 are formed on the surface of the substrate 12 such that a predetermined distance is kept between the two electrodes 16 and 18 at least in a selected region of the substrate surface. Platinum is a typical material for the electrode layers 16, 18. Lead wires connected to the electrodes 16, 18 are omitted from the illustration. The sensitive part of the gas sensor element 10 is a fired metal oxide layer 20 which is formed in the aforementioned selected region so as to fill up the gap between the two electrode layers 16 and 18 and to make close contact with the substrate surface and also with both electrode layers 16, 18 over sufficiently wide areas. The fired metal oxide layer 20 is microscopically porous and is permeable to gas molecules. The electrode layers 16, 18 are used to measure the resistance of the metal oxide layer 20. In practice, the metal oxide layer 20 and the electrode layers 16, 18 may be covered with a porous protective coating (not shown).

The principal constituent of the fired metal oxide layer 20 is a transition metal oxide represented by $TiO_2$. In the present invention, as stated hereinbefore, the material of the metal oxide layer 20 includes at least one kind of additional oxide which serves as a sintering suppressing agent and is selected from metal oxides which hardly undergo solid phase reaction with $TiO_2$, and more particularly from oxides of rare earth elements and some metal oxides having higher melting points than $TiO_2$. It is preferred to use one or any combination of $Er_2O_3$, $Sm_2O_3$ and $In_2O_3$. The amount of the sintering suppressing oxide(s) should be at least 0.01 mol % of $TiO_2$. If the amount of this oxide component is less than 0.01 mol % of $TiO_2$ it is difficult to suppress excessive sintering of the titania particles, and therefore the gas sensor element cannot noticeably be improved in the speed of response. However, it is undesirable to unnecessarily increase the amount of the sintering suppressing oxide, because the electric resistance of a metal oxide layer 20 very high in the content of sintering suppressing oxide becomes excessively high upon exposure to a gas atmosphere relatively high in the content of oxygen. For example, when the gas sensor element is used as an exhaust sensor in an air/fuel ratio feedback control system for automobiles, excessively high resistance of the metal oxide layer 20 under "lean" conditions might raise difficulty in discriminating the output of the exhaust sensor from noise signals, which will possibly obstruct accurate function of the control system. It is preferable that the amount of the sintering suppressing oxide(s) is not more than 10 mol % of $TiO_2$.

Both the speed of response of the gas sensor element and the firmness of adhesion of the metal oxide layer 20 to the substrate 12 can further be improved by adding at least one kind of noble metal selected from the metals of the platinum group to the material of the metal oxide layer 20. A suitable range of the amount of the noble metal(s) is from 0.01 to 10 mol % of $TiO_2$. When the amount of the noble metal is less than 0.01 mol % of $TiO_2$ the effects of addition of the noble metal are almost inappreciable. When the noble metal amounts to more than 10 mol % of $TiO_2$ the degree of a change in the electric resistance of the metal oxide layer 20 in response to a given change in the composition of the environmental gas atmosphere becomes considerably small so that, for example, high accuracy may not be maintained in detecting changes between a lean condition and a rich condition as an exhaust sensor in an air/fuel ratio feedback control system.

As the noble metal it is preferred to use platinum and/or rhodium. More strictly, it is preferable to use platinum or a combination of platinum and rhodium. In the latter case the addition of the noble metals is optimized by limiting the molar ratio of Rh to Pt within the range from 0.01:1 to 0.8:1.

EXAMPLES 1-3

Gas sensor elements produced as Examples 1-3 were all of the construction shown in FIGS. 1 and 2. In every example the principal material of the metal oxide layer 20 was a powder of rutile-type titanium dioxide consisting of 0.1-10 μm particles. In Example 1 the titania powder was mixed with a powder of $Er_2O_3$ amounting exactly to 1 mol % of $TiO_2$ in a liquid vehicle to thereby obtain a titania base paste. In Example 2 the same molar amount of $Sm_2O_3$ powder was used in place of the erbium oxide powder, and in Example 3 the same molar amount of $In_2O_3$ powder was used. In every example the gas sensor element 10 was produced by the following process.

To obtain the sintered alumina substrate 12 including the embedded heater 14, a platinum paste was applied onto a piece of green alumina sheet (12b) by screen printing so as to form a conductive layer (14) in a desired pattern. and another piece of green alumina sheet (12a) was placed on the paste-applied sheet (12b). Then, a platinum paste was applied by screen printing onto the green substrate (12) in the pattern shown in FIG. 2 to form the conductive layers (16, 18) as the intermediate of the electrode layers 16, 18. Next, the paste containing $TiO_2$ and one of $Er_2O_3$, $Sm_2O_3$ and $In_2O_3$ was applied by screen printing onto the green substrate (12) so as to form the oxide layer (20) which partly covered the platinum paste layers (16, 18). The reSultant green laminate was dried under usual conditions and then fired at 1400° C. for 2 hr. In the thus produced gas sensor elements the thickness of the fired metal oxide layer 20 was always slightly smaller than 100 μm. The gas sensor elements of Examples 1-3 were subjected to an evaluation test as described hereinafter. For comparison, two different kinds of gas sensor elements not in accordance with the invention were produced as References 1 and 2 by modifying the above described manufacturing process only in the following points, respectively.

REFERENCE 1

The metal oxide layer 20 was formed by using a titania paste containing no additional oxide powder.

REFERENCE 2

The metal oxide layer 20 was formed by using a titania paste containing 1 mol % of $Al_2O_3$ powder instead of a sintering suppressing oxide powder used in the present invention.

EVALUATION TEST

Figure 3:
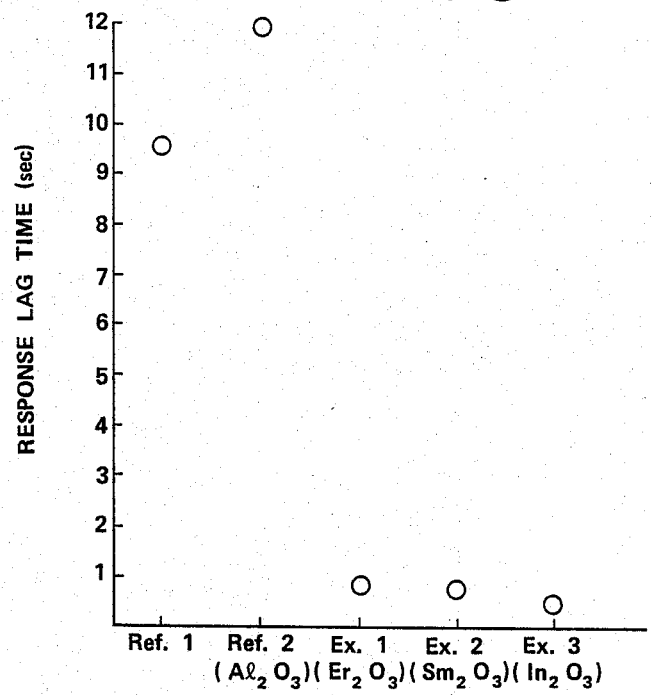
FIGS. 3-5 are charts showing the results of evaluation tests, in respect of responsiveness, on several gas sensor elements produced as examples of the invention.

The gas sensor elements of Examples 1-3 and Reference 1 and 2 were each tested in a stream of a simulated exhaust gas produced by burning propane gas. Initially the air-to-fuel ratio at the burner was controlled to about 13.3 by weight, which is representative of a fuel-rich condition in automotive internal combustion engines. Then, the air-to-fuel ratio was suddenly changed to about 16.3 representative of a lean mixture condition. In response to the change in the air-to-fuel ratio the gas sensor element under testing exhibited a sharp increase in the electric resistance of the metal oxide layer 20. There was a time lag in such response of the gas sensor element, and the length of the lag time differed from sample to sample. FIG. 3 shows the results of the evaluation test.

As is evident from FIG. 3, the addition of $Er_2O_3$, $Sm_2O_3$ or $In_2O_3$ to $TiO_2$ in Examples 1-3 produced a noticeable improvement in the speed of response of the gas sensor element. In contrast, the addition of $Al_2O_3$ in Reference 2 had rather an adverse effect on the speed of response though $Al_2O_3$ is known as a sort of sintering suppressing agent. The reason for ineffectiveness of $Al_2O_3$ in this case is presumably that the firing temperature was as high as 1400° C. At such a high temperature $Al_2O_3$ could not effectively prevent rapid progress of excessive sintering of titania particles into an undesirably tightly sintered structure. In the tested five kinds of gas sensor elements there was no indication of peel between the metal oxide layer 20 and the substrate 12.

EXAMPLES 4-7

In these examples, Pt was added to $TiO_2$ as the material of the metal oxide layer 20 besides a sintering suppressing oxide. That is, the titania powder used in Examples 1-3 was first mixed with 2 mol % of platinum powder. In Examples 4, 5 and 6 the Pt-containing titania powder was mixed in a liquid vehicle with $Er_2O_3$ powder, with $Sm_2O_3$ powder and with $In_2O_3$ powder, respectively. In every case the additional oxide amounted to 1 mol % of titania. In Example 7 the Pt-containing titania powder was mixed in the liquid vehicle with 0.5 mol % of Er powder and 0.5 mol % of $Sm_2O_3$ powder. Otherwise, the manufacturing process in Examples 1-3 was repeated.

The gas sensor elements of Examples 4-7 were subjected to the evaluation test described hereinbefore. The results are shown in FIG. 4.

REFERENCE 3

For comparison, the aforementioned mixture of the titania powder and 2 mol % of platinum powder was used as the material of the metal oxide layer 20 without addition of any sintering suppressing oxide. The resultant gas sensor element was subjected to the same evaluation test. The result is contained in FIG. 4.

Figure 4:
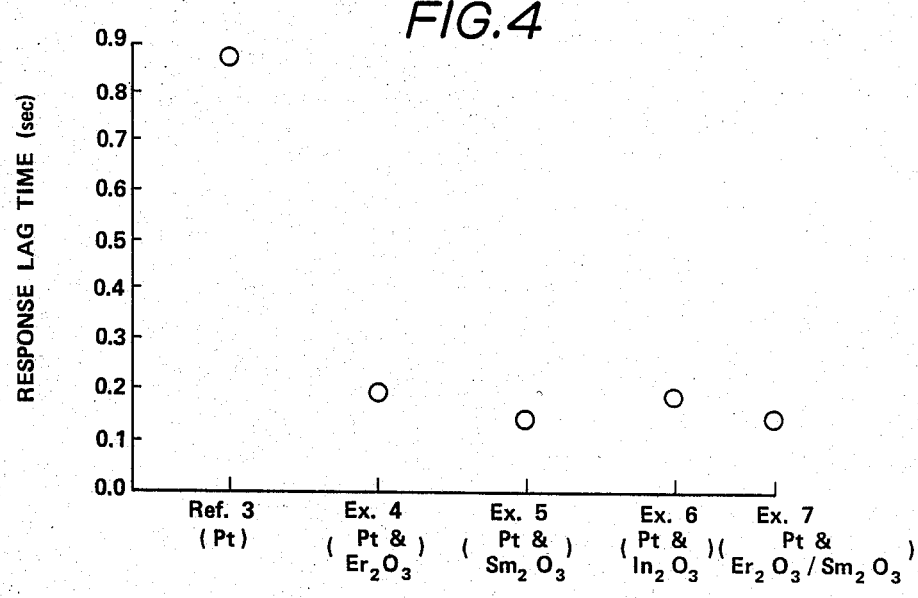

From a comparison between FIG. 3 and FIG. 4 it is apparent that the speed of response of the gas sensor element considerably improves by the existence of Pt in the metal oxide layer 20. Also it is evident that, even though the addition of Pt is so effective, yet the addition of at least one of $Er_2O_3$, $Sm_2O_3$ and $In_2O_3$ to $TiO_2$ besides the addition of Pt has a marked effect on the speed of response of the gas sensor element. In the gas sensor elements of Examples 4-7 there was no indication of peel between the metal oxide layer 20 and the substrate 12.

EXAMPLES 8-11

Examples 8-11 relate to the use of a mixture of platinum powder and rhodium powder in place of the platinum powder used in Examples 4-7. In the mixed powder, Rh amounted to 20 mol % of Pt. The mixed noble metal powder was added to the titania powder such that the total of Pt and Rh mounted to 2 mol % of $TiO_2$. Otherwise, the gas sensor elements of Examples 8, 9, 10 and 11 were produced similarly to the gas sensor elements of Examples 4, 5, 6 and 7, respectively.

The gas sensor elements of Examples 8-11 were subjected to the evaluation test described hereinbefore. For comparison, the gas sensor elements of Reference 3 and Example 4 were also tested simultaneously. The results are shown in FIG. 5.

Figure 5:
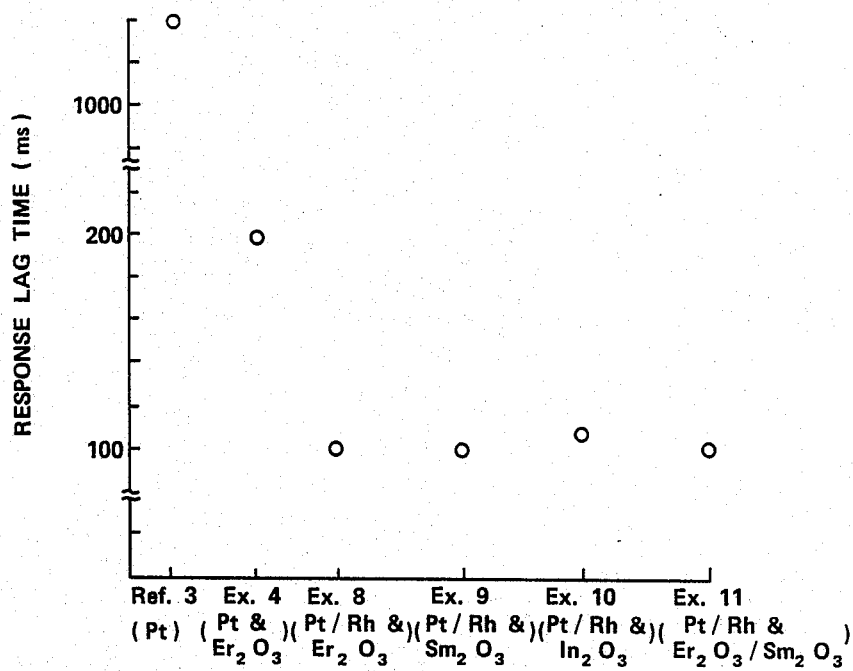

From a comparison between FIG. 4 and FIG. 5, it is understood that the favorable effect of the presence of a noble metal in the metal oxide layer 20 can be enhanced by jointly using Pt and Rh in a suitable proportion.

Figure 6:
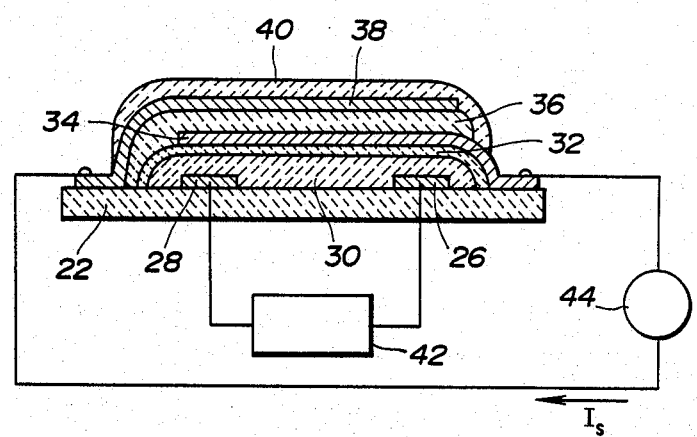
FIG. 6 is a schematic illustration, in a sectional view, of an air/fuel ratio detecting device in which the present invention is utilized.

The gas sensor element construction shown in FIGS. 1 and 2 can be modified in various ways, and the present invention is applicable for various purposes. For example, FIG. 6 shows the use of this invention in an air/fuel ratio detecting device disclosed in U.S. Pat. No. 4,416,763.

The device of FIG. 6 includes a gas sensor element according to the invention, which is comprised of an insulating substrate 22, a pair of electrode layers 26 and 28 formed on the same side of the substrate 22 and a fired metal oxide layer 30 which is formed so as to substantially entirely cover the electrode layers 26, 28 and to fill up the 9ap between the two electrodes 26 and 28. The principal material of the metal oxide layer 30 is $TiO_2$, and at least one of $Er_2O_3$, $Sm_2O_3$ and $In_2O_3$ is added preferably together with Pt and/or Rh. The metal oxide layer 30 is microscopically porous. The outer surface of the metal oxide layer 30 is covered with a porous insulating layer 32.

An electrode layer 34 is laid on the surface of the insulating layer 32, and a layer 36 of an oxygen ion conductive solid electrolyte such as $ZrO_2$ containing a stabilizing oxide such as CaO or $Y_2O_3$ is formed so as to cover a substantial area of the electrode layer 34. Another electrode layer 38 is laid on the outer surface of the solid electrolyte layer 36. The three layers 34, 36 and 38 are all microscopically porous and permeable to gases. The outer surfaces of the laminate are covered with a porous protective coating layer 40. Indicated at 42 is an ohmmeter to measure the resistance of the metal oxide layer 30 between the two electrodes 26 and 28, and at 44 is DC power source to which the electrodes 34 and 38 are connectable.

This device is used in the exhaust line of an internal combustion engine to detect a change in the air/fuel ratio in the engine. As is known the combination of the solid electrolyte layer 36 and the inner and outer electrode layer 34 and 38 serves as either an oxygen concentration cell or an oxygen ion pump. While the electrodes 34 and 38 are not connected to any power source the three layers 38, 36, 34 serve merely as gas diffusion layers, so that the device of FIG. 6 does not functionally differ from the gas sensor element 10 of FIG. 1. In that state, there occurs a sharp change in the resistance of the metal oxide layer 30 if the air/fuel ratio in the engine combustion chambers changes across the stoichiometric value. When the DC power source 44 is used to force a weak DC current $I_s$ to flow through the solid electrolyte layer 36 the combination of the solid electrolyte layer 36 and the electrode layers 34, 38 acts as an oxygen ion pump. If the current $I_s$ flows in the direction of the arrow in FIG. 6 the oxygen ion pump functions so as to decrease the quantity of oxygen diffusing into the metal oxide layer 30 because the current $I_s$ causes oxygen ions to migrate toward the outer electrode layer 38. In such state, the resistance of the metal oxide layer 30 sharply changes only when the air/fuel ratio in the engine changes across a specific value which is higher than the stoichiometric value and is determined by the magnitude of the current $I_s$. Therefore, the device of FIG. 6 becomes useful in a so-called lean-burn engine. When the current $I_s$ flows in the reverse direction the same device becomes useful in an engine operated with a fuel-rich mixture.

To produce the multilayered device of FIG. 6 with strong adhesion of each layer to either the substrate 22 or the adjacent layers, it is desirable to laminate all the layers in the green state and to simultaneously fire all the layers at a relatively high temperature. Accordingly, the introduction of a sintering suppressing oxide into the titania base metal oxide layer 30 according to the invention is very favorable for this multilayered device.

What is claimed is:

1. A gas sensor element comprising:
    a ceramic substrate; and
    a mixture of titanium dioxide and a sintering suppressing agent laminated on said ceramic substrate, said agent comprising at least one additional metal oxide selected from the group consisting of $Er_2O_3$ and $Sm_2O_3$.

2. A gas sensor element according to claim 1, wherein the total amount of said at least one additional metal oxide is in the range from 0.01 to 10 mol % of said titanium dioxide.

3. A gas sensor element according to claim 1, wherein said mixture further comprises at least one noble metal of the platinum group.

4. A gas sensor element according to claim 3, wherein the total amount of said at least one noble metal is in the range from 0.01 to 10 mol % of said titanium dioxide.

5. A gas sensor element according to claim 4, wherein said at least one noble metal consists of Pt.

6. A gas sensor element according to claim 4, wherein said at least one noble metal is a combination of Pt and Rh, the molar ratio of said Pt to said Rh being in the range from 1:0.01 to 1:0.8.

7. A gas sensor element according to claim 1 wherein said ceramic substrate is alumina.

8. A gas sensor element according to claim 1, wherein said mixture consists essentially of titanium dioxide and said sintering agent.

9. A gas sensor element according to claim 1, wherein said ceramic substrate has a sintering temperature of about 1300° to 1400° C.

10. A gas sensor element according to claim 1, wherein said at least one additional metal oxide is present in an amount sufficient to suppress sintering at temperatures above about 1200° C. to an extent sufficient to improve gas permeability of sintered titanium dioxide.

11. A sintered exhaust sensor for monitoring the air-fuel ratio of an internal combustion engine comprising:
    a ceramic substrate; and
    a mixture of titanium dioxide and a sintering suppressing agent laminated on said substrate, wherein said sintering suppressing agent is selected from the group consisting of $Er_2O_3$ and $Sm_2O_3$.

12. An exhaust sensor according to claim 11, wherein the total amount of said agent is in the range from 0.01 to 10 mol % of said titanium dioxide.

13. An exhaust sensor according to claim 11, wherein said mixture further comprises at least one noble metal of the platinum group.

14. An exhaust sensor element according to claim 11, wherein said ceramic substrate is alumina.

15. An exhaust sensor according to claim 11, wherein said mixture consists essentially of titanium dioxide and said sintering agent.

16. An exhaust sensor according to claim 11, wherein said ceramic substrate has a sintering temperature of about 1300° to 1400° C.

17. A gas sensor element comprising titanium dioxide and a sintering suppression agent selected from the group consisting of $Er_2O_3$ and $Sm_2O_3$.

* * * * *